United States Patent [19]

McCombs

[11] 4,329,294
[45] May 11, 1982

[54] PROCESS FOR PREPARING 17α-HYDROXY-20-KETOSTEROIDS

[75] Inventor: Charles A. McCombs, Kingsport, Tenn.

[73] Assignee: Eastman Kodak Company, Rochester, N.Y.

[21] Appl. No.: 247,951

[22] Filed: Mar. 26, 1981

[51] Int. Cl.$^3$ ............................................... C07J 1/00
[52] U.S. Cl. ............................. 260/397.4; 260/397.45
[58] Field of Search ........................ 260/397.4, 397.45

[56] References Cited

PUBLICATIONS

"Gardner et al.", *The Journal of Organic Chemistry,* (1968), No. 33, pp. 3294–3297.

Primary Examiner—Elbert L. Roberts
Attorney, Agent, or Firm—Clyde L. Tootle; Daniel B. Reece, III

[57] ABSTRACT

In accordance with the present invention, 17α-hydroxy-20-ketosteroids are prepared by the oxidation of 20-ketosteriods, such as 3-methoxy-pregna-3,5-dien-20-one. The 3-methoxypregna-3,5-dien-20-one is prepared from progesterone by methods well known in the art. The pregn-20-ones, such as 3-methoxypregna-3,5-dien-20-one, are oxidized with oxygen or air using a base catalyst in the presence of a phosphite reducing agent in a suitable solvent. The base catalyst consists of an alkali metal tert-alkoxide, which can be prepared from an alkali metal and a tert-alkanol. The oxidation reaction can be carried out at any temperature from about −20° C. to about 50° C. and for a period of 2–20 hours depending on the temperature at which the reaction is carried out. For example, at ambient temperature the rate of oxidation is sufficiently fast to complete the oxidation in 2 to 4 hours. This method for preparing 17α-hydroxy-20-ketosteroids from 20-ketosteroids is an important and valuable step in preparing corticosteroids and other hormones.

12 Claims, No Drawings

PROCESS FOR PREPARING 17α-HYDROXY-20-KETOSTEROIDS

This invention relates to a novel process for preparing 17α-hydroxy-20-ketosteroids by the oxidation of the corresponding 20-ketosteroid, such as 3-methoxypregna-3,5-dien-20-one.

The direct introduction of a hydroxyl group at the 17 position of progesterone, protected as its Δ³,⁵ methyl enol ether, would be a valuable process for the synthesis of 17α-hydroxyprogesterone, and could be readily adapted to other corticosteroid intermediates. Unfortunately, this oxidation has heretofore been a poor process. D. Barton [J. Chem. Soc., 1578(1962)] developed a method for the hydroperoxylation of the 17(20)-enolate of 3-ethoxypregna-3,5-dien-20-one using oxygen and potassium and tert-butyl alcohol, dimethylformamide (DMF), and tetrahydrofuran (THF). The intermediate hydroperoxide was isolated in 30% yield and hydrolyzed to 17α-hydroperoxyprogesterone in 75% yield. This process was ultimately improved when J. Garnder [J. Org. Chem., 33, 3294(1968)] found that the addition of trialkylphosphites reduced the intermediate hydroperoxide to the alcohol in situ and was stable to the reaction conditions. Gardner used his modifications of the Barton procedure to oxygenate pregnen-20-ones to their 17α-hydroxy compounds; in a similar fashion, pregnan-20-ones, were converted in yields between 60–70%.

Unfortunately, the Barton procedure with the Gardner modification failed to give even a trace of 17α-hydroxy-3-methoxypregna-3,5-dien-20-one by oxygenation of 3-methoxypregna-3,5-dien-20-one using several variations of the solvent ratio and reaction conditions.

It would therefore be a significant advance in the state of the art to provide a simple high yield process for the preparation of 17α-hydroxy-20-ketosteroids from their corresponding 20-ketosteroid by direct oxidation.

In accordance with the present invention, 17α-hydroxy-20-ketosteroids are prepared in high yields by the oxidation of 20-ketosteroids, such as 3-methoxypregna-3,5-dien-20-one. The 3-methoxypregna-3,5-dien-20-one is prepared from progesterone by methods well known in the art. One such method uses dimethoxypropane in dimethylformamide with an acid catalyst as reported by A. L. Nassbaum et al., J. Org. Chem., 26, 3925 (1961). The 3-methoxypregna-3,5-dien-20-one is oxidized with air or oxygen using a base catalyst in the presence of a phosphite reducing agent in a suitable solvent. The base catalyst consists of an alkali metal tert-alkoxide which can be prepared from an alkali metal and a tert-alkanol. The oxidation reaction can be carried at any temperature from about −20° C., to about 50° C. and for a period of 2–20 hours depending on the temperature at which the reaction is carried out. For example, at ambient temperature the rate of reaction is sufficiently fast to complete the oxidation in 2 to 4 hours.

Suitable solvents are polar, nonprotic solvents such as, for example, dimethylformamide, tetrahydrofuran and the like with an alkanol. Generally, the alkanol employed is the same alkanol used in preparing the alkoxide catalyst. Such alkanols include $C_5$ to $C_{12}$ tert-alcohols, such as tert-pentyl alcohol, tert-hexyl alchol, tert-heptyl alcohol, tert-octyl alcohol, and the like. The solvent contains nonprotic solvent in an amount of 50 to 100 percent, by weight, preferably 75 to 95 percent, by weight to the alkanol. The solvent is used in an amount, based on the weight of the steroid, of about 3 to 50 times by weight, preferably about 30 to 50 times. The use of the lower ratios 3 to 30 depends on the solubility of the reagents involved in the reaction.

The alkali metal alkoxide can be sodium tert-pentylate, potassium tert-pentylate, as well as salts of higher tert-alkanols, and the like. The amount of alkali metal alkoxide used is about 1.0 to 3.0 moles alkoxide per mole to steroid.

The phosphite reducing agent can be any suitable reducing agent such as, for example, trimethyl phosphite, ethyl dimethyl phosphite, methyl diethyl phosphite, triethyl phosphite and the like.

The 17α-hydroxy-20-ketosteroid can be separated and isolated, for example, by extraction with a suitable solvent such as methylene chloride. The extract can be dried over anhydrous sodium sulfate and the solvent evaporated to provide the 17α-hydroxy steroid.

This invention can be further illustrated by the following examples, although it will be understood that these examples are included merely for purposes of illustration and are not intended to limit the scope of the invention unless otherwise specifically indicated.

EXAMPLE 1

To a solution of 50 ml of 0.60 M sodium tert-pentylate in tert-pentyl alcohol was added 3-methoxypregna-3,5-dien-20-one (5.0 g, 15.2 mmole), trimethylphosphite (2.8 g, 20.8 mmole) and 200 ml dry dimethylformamide. With initial ice bath cooling, oxygen was introduced via two submerged gas inlets for two hours. The resulting red solution was poured into one liter of ice/water and extracted twice with 350 ml methylene chloride. The organic extracts were combined, dried over anhydrous sodium sulfate, and evaporated to remove solvent and residual dimethylformamide. The resulting yellow solid, melting point 170°–180° C., was difficult to recrystallize, but exhibited totally consistent spectral data for 17α-hydroxy-3-methoxypregna-3,5-dien-20-one and was identical with an authentic sample by NMR, IR, MS, and TLC mobility. The authentic sample was prepared from 17α-hydroxyprogesterone according to a procedure by M. J. Weiss [Tetrahedron, 20, 357(1964)].

The crude enol ether was dissolved in a minimum amount of acetone and mixed with an equal volume of 2% aqueous hydrochloric acid for one hour. The solution was then diluted twenty-fold with water and extracted twice with 200 ml of methylene chloride. The combined extracts were eluted through a 6″×1″ column of silica gel (70–230 mesh) without fractionation. The column was further eluted with 100 ml methylene chloride to completely elute product away from residual gums. After evaporation of the eluant, 3.74 (75%) of 17α-hydroxyprogesterone was obtained as an off-white solid. An analytical sample with melting point 212°–215° C. was obtained by preparative TLC and was identical with an authentic sample by NMR, IR, MS, and TLC mobility.

In addition, the enol ether need not be isolated as identical yields of 17α-hydroxyprogesterone were obtained by pouring the reaction mixture into water, acidification, extraction, and elution through silica gel.

EXAMPLE 2

11-Keto-17α-hydroxyprogesterone

11-Keto-3-methoxypregna-3,5-dien-20-one, which was prepared from 11-ketoprogesterone, was treated with sodium tert-pentylate and oxygen under analogous conditions. The resulting 11-keto-17α-hydroxy-3-methoxypregna-3,5-dien-20-one could be isolated to afford a yellow solid, melting point 230°–232° C. (dec), which was hydrolyzed to 11-keto-17α-hydroxy-progesterone, melting point 175°–90° C. (dec), in 26% overall yield. This low yield was due to water solubility in aqueous acetone, and not optimized.

In addition, other pregnen-20-ones, pregnan-20-ones, and 21-desoxycorticosterones can be converted to their corresponding 17α-hydroxy-20-ketosteroids by the method described herein.

The process of the present invention provides a method for the high yield synthesis of 17α-hydroxy-20-ketosteroids from readily available 20-ketosteroids. This method for preparing 17α-hydroxy-20-ketosteroids by the oxidation of 20-ketosteroids is an important and valuable step in preparing corticosteroids.

I claim:

1. A process for preparing 17α-hydroxy-20-ketosteroids from 20-ketosteroids which comprises oxidizing pregn-20-one with air or oxygen using a base catalyst in the presence of a tri-lower alkyl phosphite reducing agent in a suitable solvent consisting essentially of at least one polar, nonprotic component selected from the group consisting of dimethylformamide and tetrahydrofuran and at least one $C_5$ to $C_{12}$ tert-alcohol, said $C_5$ to $C_{12}$ tertalcohol being present in said solvent in an amount of 5 to 50 weight percent.

2. A process according to claim 1 wherein said base catalyst is sodium tert-pentylate.

3. A process according to claim 2 wherein said phosphite reducing agent is trimethyl phosphite.

4. A process according to claim 3 wherein said solvent is dimethylformamide.

5. A process for reacting 3-methoxypregna3,5-dien-20-one with air or oxygen using a base catalyst in the presence of a phosphite reducing agent in a suitable solvent to prepare 17α-hydroxy-3-methoxy-3,5-dien-20-one.

6. A process according to claim 5 wherein said base catalyst is sodium tert-pentylate.

7. A process according to claim 5 wherein said solvent is dimethylformamide.

8. A process according to claim 5 wherein said phosphite reducing agent is trimethyl phosphite.

9. A process for reacting 11-keto-3-methoxypregn-3,5-dien-20-one with air or oxygen using a base catalyst in the presence of a tri-lower alkyl phosphite reducing agent in a suitable solvent to prepare 17α-hydroxy-11-keto-3-methoxypregna-3,5-dien-20-one, said solvent consisting essentially of at least one polar, nonprotic component selected from the group consisting of dimethylformamide and tetrahydrofuran and at least one $C_5$ to $C_{12}$ tert-alcohol, said $C_5$ to $C_{12}$ tert-alcohol being present in said solvent in an amount of 5 to 50 weight percent.

10. A process according to claim 9 wherein said base catalyst is sodium tert-pentylate.

11. A process according to claim 10 wherein said phosphite reducing agent is trimethylphosphite.

12. A process according to claim 11 wherein said solvent is diemthylformamide.

* * * * *